United States Patent
Qi et al.

(10) Patent No.: US 12,427,208 B2
(45) Date of Patent: Sep. 30, 2025

(54) IODINATED PHENOLIC LIPIDS AND METHODS AND COSOLVENT SYSTEMS FOR IODINATION OF PHENOLIC LIPIDS

(71) Applicant: University Of Cincinnati, Cincinnati, OH (US)

(72) Inventors: Xiaoyang Qi, Cincinnati, OH (US); Koon Yan Pak, Malvern, PA (US); Brian D. Gray, Malvern, PA (US)

(73) Assignees: University of Cincinnati, Cincinnati, OH (US); Molecular Targeting Technologies, Inc., West Chester, PA (US)

( * ) Notice: Subject to any disclaimer, the term of this patent is extended or adjusted under 35 U.S.C. 154(b) by 816 days.

(21) Appl. No.: 16/090,371

(22) PCT Filed: Mar. 31, 2017

(86) PCT No.: PCT/US2017/025407
§ 371 (c)(1),
(2) Date: Oct. 1, 2018

(87) PCT Pub. No.: WO2017/173288
PCT Pub. Date: Oct. 5, 2017

(65) Prior Publication Data
US 2019/0111161 A1 Apr. 18, 2019

Related U.S. Application Data

(60) Provisional application No. 62/317,051, filed on Apr. 1, 2016.

(51) Int. Cl.
*A61K 51/04* (2006.01)
*A61K 51/12* (2006.01)
*C07B 59/00* (2006.01)
*C07D 209/14* (2006.01)
*C07D 403/06* (2006.01)

(52) U.S. Cl.
CPC ...... *A61K 51/0446* (2013.01); *A61K 51/1234* (2013.01); *C07B 59/002* (2013.01); *C07D 209/14* (2013.01); *C07D 403/06* (2013.01); *C07B 2200/05* (2013.01)

(58) Field of Classification Search
CPC ............ A61K 51/1234; A61K 51/0446; A61K 49/0019; A61K 49/0021; A61K 49/005
See application file for complete search history.

(56) References Cited

U.S. PATENT DOCUMENTS 5,665,328 A    9/1997    Horan et al.

FOREIGN PATENT DOCUMENTS

WO     2005054856 A1     6/2005
WO     WO-2013181119 A1 * 12/2013 ......... G01N 33/5005

OTHER PUBLICATIONS

European Patent Office, International Search Report and Written Opinion issued in corresponding PCT Application No. PCT/US2017/025407, mailed on Aug. 31, 2017 (21 pages).
Zhou, Y et al., A cyanine-modified upconversion nanoprobe for NIR-excited imaging of endogenous hydrogen peroxide signaling in vivo, Biomaterials, vol. 54, Mar. 29, 2015, pp. 34-43.
Andrews, J et al., Characterization of excited states of centrosymmetric and noncentrosymmetric squaraines by third-harmonic spectral dispersion, Journal of the Optical Society of America—B, vol. 12, No. 12, Dec. 1, 1995, p. 2360-2371.
Miyata, A et al., Aggregates in Langmuir-Blodgett Films of Spiropyrans Having Hydroxyl or Hydroxymethyl Group, Bulletin of the Chemical Society of Japan, vol. 64, No. 6, Jun. 1, 1991, pp. 1719-1725.
Hachisako, H et al., Determination of critical aggregation concentrations of self-assembling lipids in nonpolar organic media using, Chemistry Letters (11), 1999, pp. 1165-1166.
Blanco, VM et al., Optical and nuclear imaging of glioblastoma with phosphatidylserine-targeted nanovesicles, Oncotarget, vol. 7, No. 22, Apr. 16, 2016, pp. 32866-32875.
Arcadi, A et al., Synthesis of New Cardanol Derivatives through Combined Iodination/Palladium-Catalysed Cross-Coupling Reactions, Synthesis, vol. 2006, No. 15, Aug. 1, 2006, pp. 2523-2530.

* cited by examiner

*Primary Examiner* — James W Rogers
(74) *Attorney, Agent, or Firm* — Wood Herron & Evans LLP

(57) ABSTRACT

Compositions that include a phenol group conjugated to a lipid group to form a phenolic lipid. The lipid group may include a fluorophore and at least one lipid anchor. The lipid anchor may have a carbon number that ranges between 7 carbon atoms and 22 carbon atoms. Also, included are methods of making and using such phenolic lipids. Further included are methods of iodinating hydrophobic compounds such as phenolic lipids in aqueous based iodination protocols. Cosolvent formulations for use in such methods are also described.

6 Claims, 9 Drawing Sheets

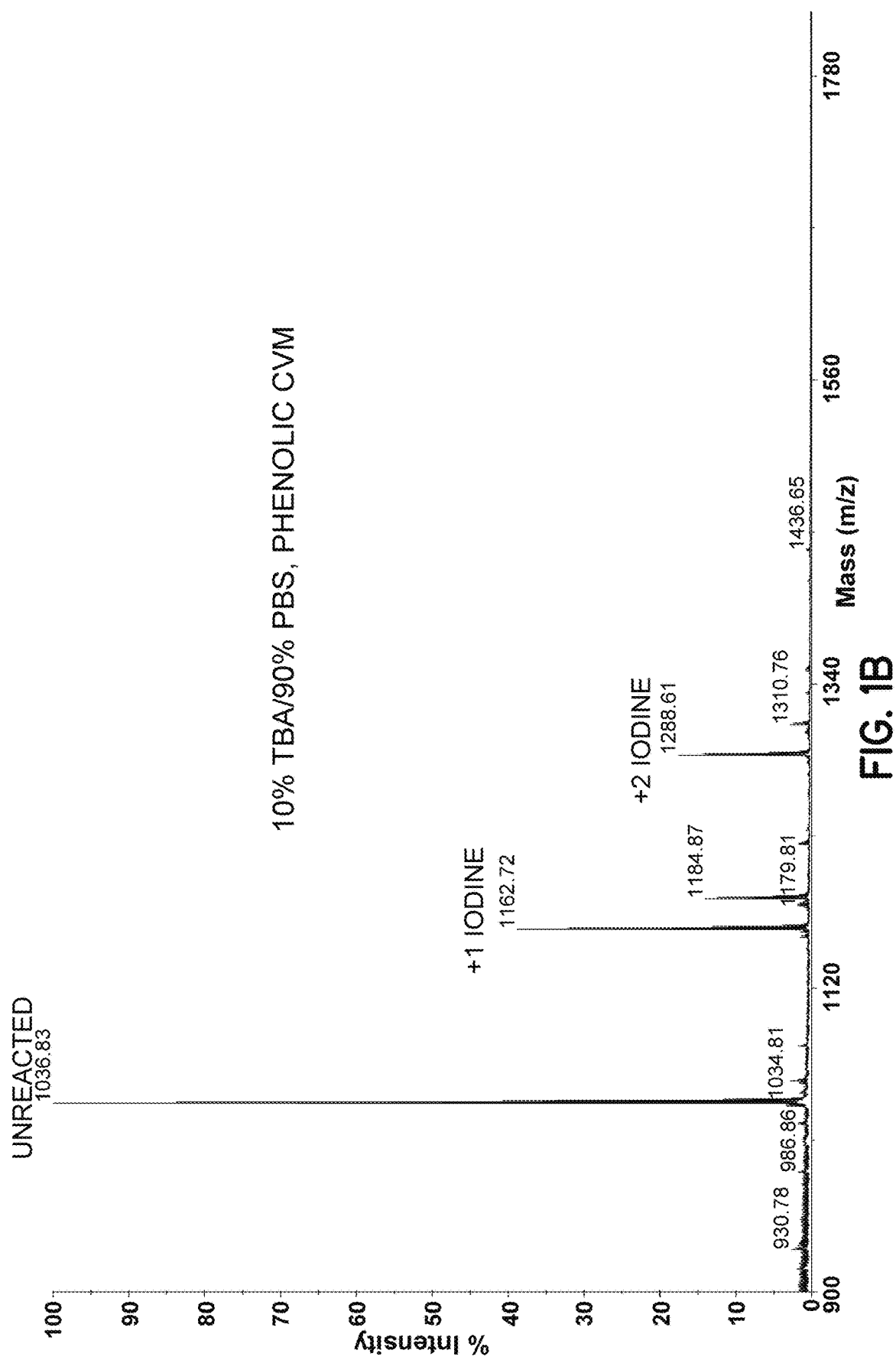

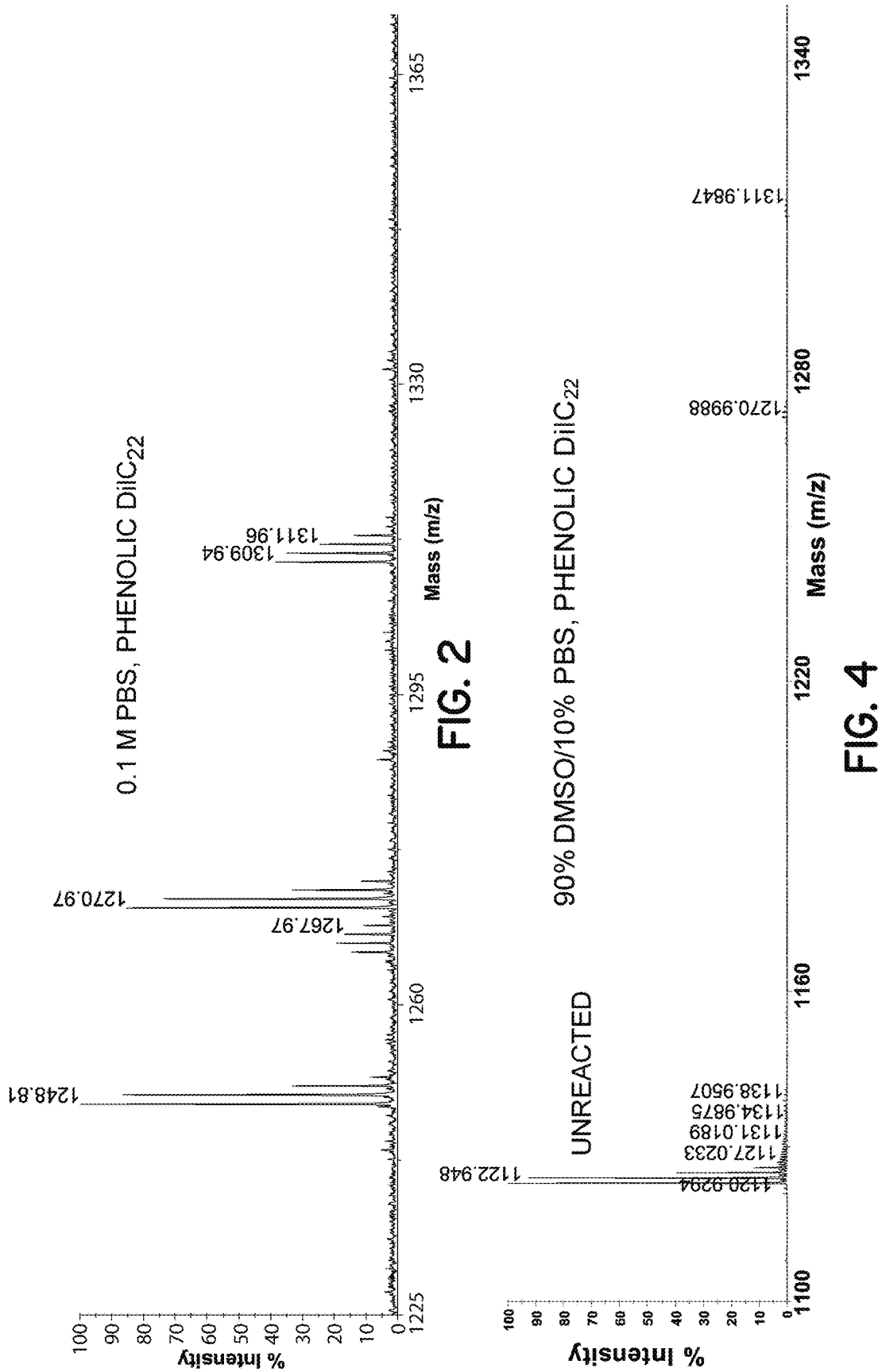

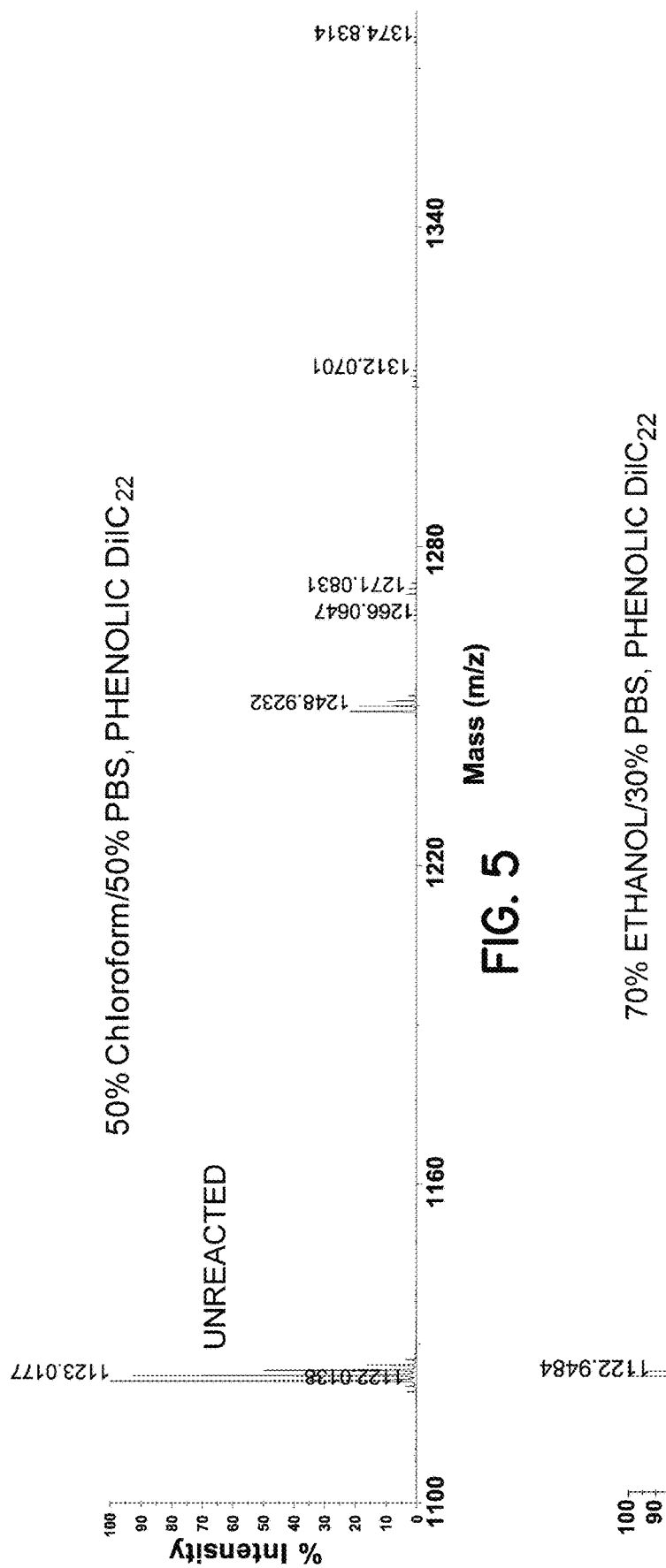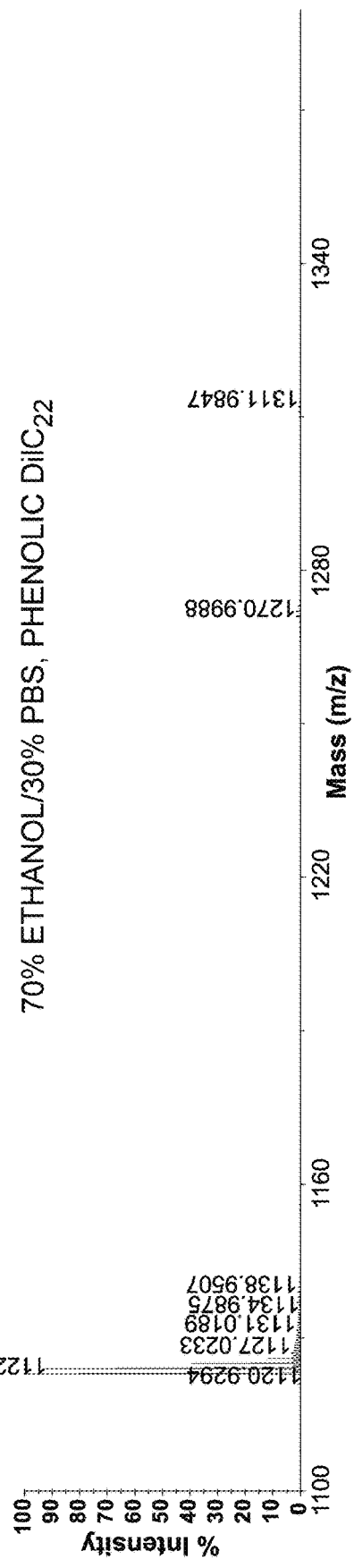

IODINATED PHENOLIC LIPIDS AND METHODS AND COSOLVENT SYSTEMS FOR IODINATION OF PHENOLIC LIPIDS

CROSS-REFERENCE TO RELATED APPLICATIONS

This application is a national stage application under 35 U.S.C. § 371 of International Application No. PCT/US2017/025407, filed on Mar. 31, 2017, which claims priority to U.S. Provisional Application No. 62/317,051 filed Apr. 1, 2016, the disclosures of which are hereby incorporated by reference herein in their entireties.

FIELD

The present invention relates generally to iodinated phenolic lipids and methods and cosolvent compositions for iodination of phenolic lipids.

BACKGROUND

Iodination is the covalent coupling of iodine to a molecule. Iodination of aromatic rings in organic molecules is routinely accomplished utilizing an oxidizer. Strong oxidizers can damage complex organic molecules, such as proteins, peptides, nucleic acids, and lipids. Accordingly, mild oxidizers have been developed as iodination reagents for use with complex organic molecules. One such iodination reagent is 1,3,4,6-tetrachloro-3α, 6α-diphenylglycouracil, which is insoluble in aqueous media. This iodination reagent is typically coated onto the walls of a reaction tube prior to conducting the iodination reaction.

During a typical iodination reaction utilizing a pre-coated iodination tube, a sample of organic molecules is suspended in an aqueous media with a source iodide ions, such as an iodide salt. The mixture is then incubated in the pre-coated iodination tube for a period of time sufficient for the oxidation reaction to result in the desired level of iodination of the organic molecules. Since the iodination reagent is insoluble in most aqueous media, it remains adherent to the walls of the tube during the iodination reaction allowing the iodination reaction to be terminated by simply decanting the sample from the tube.

This method is particularly useful with organic molecules that are soluble in aqueous media, such as proteins, peptides, and nucleic acids, as well as for iodinating lipids on the surface of a cell membrane that are exposed in aqueous environments. This method is not generally useful to efficiently iodinate organic molecules that are insoluble in aqueous media.

Phenolic lipids are amphiphilic molecules that have a hydrophobic lipid portion and a hydrophilic phenol portion. Phenolic lipids are subject to iodination on the phenol portion, but because phenolic lipids are largely insoluble in aqueous media, they have previously been incapable of iodination with aqueous-based iodination protocols, such as those employing pre-coated iodination tubes. Methods of iodinating hydrophobic phenolic lipids using aqueous-based iodination protocols are needed.

SUMMARY

An aspect of the invention is directed to phenolic lipids. Another aspect is directed methods of treating a disease, such as a cancer, with a phenolic lipid, and in particular with an iodinated phenolic lipid. Another aspect of the invention addresses issues with iodinating hydrophobic compounds using aqueous based iodination methods and in particular issues with iodinating phenolic lipids using aqueous based iodination protocols, such as protocols employing pre-coated iodination tubes. Another aspect of the invention is directed to cosolvent compositions for iodinating phenolic lipids using aqueous iodination protocols as well as iodinated phenolic lipids.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 1B is a tracing from the mass spectrometry analysis of a phenolic lipid iodinated in a cosolvent composition having a 90:10 PBS to TBA (vol:vol) ratio in accordance with embodiments of the invention.

FIG. 2 is a tracing from the mass spectrometry analysis of a phenolic lipid iodinated in a cosolvent composition having a 75:25 PBS to TBA (vol:vol) ratio in accordance with embodiments of the invention.

FIG. 4 is a tracing from the mass spectrometry analysis of a phenolic lipid processed with a protocol utilizing a cosolvent that included 90% DMSO and 10% PBS.

FIG. 5 is a tracing from the mass spectrometry analysis of a phenolic lipid processed with a protocol utilizing a cosolvent that included 50% chloroform and 50% PBS.

FIG. 6 is a tracing from the mass spectrometry analysis of a phenolic lipid processed with a protocol utilizing a cosolvent that included 70% ethanol and 30% PBS.

DETAILED DESCRIPTION

Figure 1A:
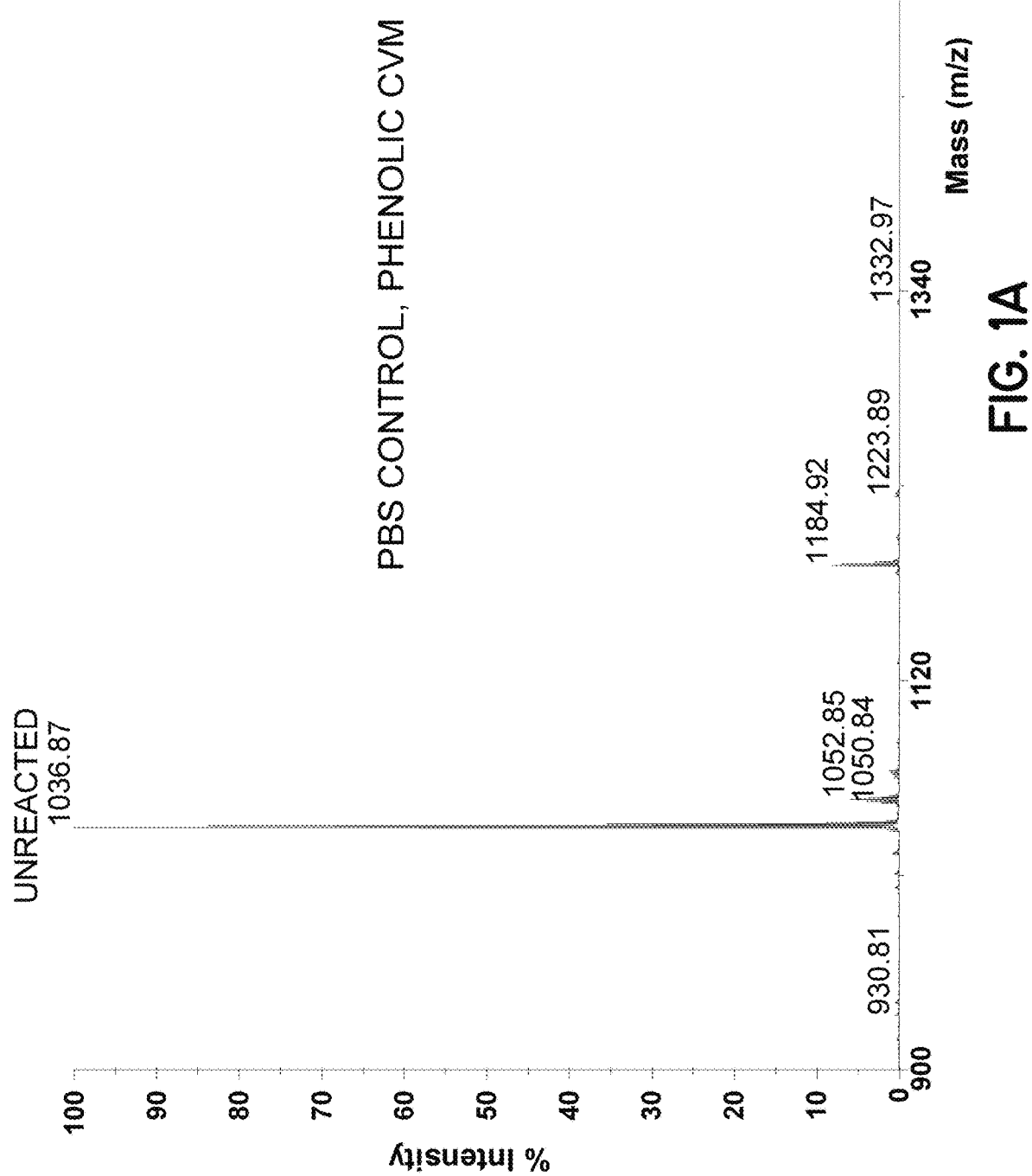
FIG. 1A is a tracing from the mass spectrometry analysis of a phenolic lipid suspended in PBS without a cosolvent.

Broader aspects of the invention are directed to phenolic lipids, methods of treating diseases with phenolic lipids, and methods and composition for iodinating phenolic lipids and other compounds that are not typically soluble in aqueous media using aqueous-based iodination protocols.

Phenolic lipids have a hydrophobic lipid group and a hydrophilic phenol group. Phenolic lipids are subject to iodination on the hydrophilic phenol group. However, phenolic lipids tend to be largely insoluble in aqueous media and are thus not typically capable of being iodinated using aqueous-based iodination protocols. An aspect of the invention described herein is directed to a cosolvent composition that is capable of both solubilizing phenolic lipids and resulting in the iodination of the phenolic lipid in aqueous-based iodination protocols. Another aspect of the invention is a method of iodinating phenolic lipids utilizing the cosolvent composition in an aqueous-based iodination protocol.

The cosolvent composition is comprised of an alcohol portion and an aqueous portion. The alcohol portion has at least three carbon atoms and is miscible in the aqueous portion over at least part of the volume to volume ratio of the aqueous portion to alcohol ranging from about 90:10 to about 10:90. The alcohol portion must also solubilize the phenolic lipid when mixed with the aqueous portion and result in the iodination of at least a portion of the solubilized phenolic lipids when used in an aqueous-based iodination protocol. In an embodiment, the alcohol has three or four carbon atoms or a mixture of alcohols having three or four carbon atoms. Exemplary preferred alcohols are tert-butyl alcohol and isopropyl alcohol, which may be used individually or in combination.

The aqueous portion includes at least water. The aqueous portion may also include one or more salts, one or more buffers, or combinations of salts and buffers. Exemplary aqueous portions include, phosphate buffer, phosphate buffered saline (PBS), Tris buffered saline, Ringer's solution, and lactated Ringer's solution.

The volume to volume ratio of the aqueous portion to the alcohol portion can range from about 90:10 to about 10:90. In an embodiment, the volume to volume ratio ranges from about 75:25 to about 25:75 and alternatively ranges from about 60:40 to about 40:60. In another embodiment, the volume to volume ratio of the aqueous portion volume to alcohol volume is about 50:50.

The cosolvent composition may also include iodide ion in a range from about 0.01 mM to about 10 mM, and in an embodiment, is present at about 1 mM. The iodide ion may originate from an iodide salt, such as sodium iodide, potassium iodide, and combinations thereof. In an embodiment, the iodide ion is a radioisotope, such as I-123, I-124, I-125, I127, I-131, or combinations thereof. The composition may include the radioisotope of iodide in a range from about 0.05 mCi to about 2 mCi per 100 micrograms of phenolic lipid to be labeled, and alternatively, in a range from about 0.1 mCi to about 1 mCi per 100 micrograms of phenolic lipid to be labeled.

The iodide ion in buffer solution is typically added to an iodination reaction tube before adding the phenolic lipid which has been suspended in the cosolvent composition. In the alternative, the iodide ion may be mixed with the phenolic lipid suspension before adding into an iodination reaction tube. In another alternative, the iodide ion may be mixed with the cosolvent composition proximate in time to the use of the composition in an iodination reaction, and preferably after the phenolic lipid has been suspended in the cosolvent composition.

The cosolvent composition may be utilized to iodinate phenolic lipids. Accordingly, an aspect of the invention is directed to phenolic lipids, i.e., at least one phenol group coupled to at least one lipid. Of particular interest are phenolic lipids that have a lipid portion that includes a fluorophore coupled to at least one lipophilic anchor, and preferably a pair of lipophilic anchors. Exemplary lipophilic anchors include saturated hydrocarbons having from 7 to 22 carbon atoms. Additional exemplary lipophilic anchors include unsaturated hydrocarbon having from 7 to 22 carbon atoms. Examples of other lipids that could be phenolated and ultimately iodinated for use in aspects of the present invention are described in U.S. Pat. No. 5,665,328, which is incorporated herein in its entirety. Another exemplary phenolic lipid is a phenolic carbocyanine dye. An exemplary phenolic carbocyanine dye includes an indocarbocyanin iodide head group couple to two saturated hydrocarbon chains having between 7 and 22 carbon atoms. Another exemplary phenolic carbocyanine dye includes an indocarbocyanin iodide head group couple to one saturated hydrocarbon chain and one unsaturated hydrocarbon chain or two unsaturated hydrocarbon chains, wherein the hydrocarbon chains have between 7 and 22 carbon atoms. In an embodiment, both hydrocarbon chains have the same number of carbon atoms and in an exemplary embodiment, the hydrocarbon chain has 22 carbon atoms, which is referred to herein as phenolic $DilC_{22}$. In another embodiment, the hydrocarbon chains have different numbers of carbon atoms and in an exemplary embodiment, the first carbon chain has 7 carbon atoms and the second carbon chain has 22 carbon atoms, which is referred to herein as $DilC_{14,22}$.

The phenolic lipids may be synthesized as known in the art. In an embodiment, phenolic $DilC_{22}$ is prepared from amino-$DilC_{22}$. Amino-$DilC_{22}$ was prepared as previously described [Kopia et al. U.S. Pat. No. 5,667,764] and coupled with 3-(4-hydroxyphenyl)propionic acid (Sigma, St Louis) in the presence of N,N,N',N'-Tetramethyl-O-(1H-benzotriazol-1-yl)uroniumhexafluorophosphate(HBTU) in DMF containing triethylamine (Synthetic Pathway 1 below). After stirring at room temperature for 24 h, the mixture was concentrated and purified by silica gel chromatography eluting with increasing amounts of methanol (1% to 5%) in dichloromethane (59% yield). 400 MHz proton NMR (CDCl3): 8.41 (t, 1H), 7.42 (m, 2H), 7.10 (m, 2H), 7.03 (m, 2H), 6.75 (d, 2H), 6.30 (m, 2H), 6.20 (m, 1H), 6.0 (m, 1H), 4.40 (d, 2H), 4.05 (m, 4H), 2.91 (m, 2H), 2.55 (m, 2H), 1.90 1.60 (m), 1.5-1.2 (m), 0.90 (t, 6H).

Synthetic Pathway 1

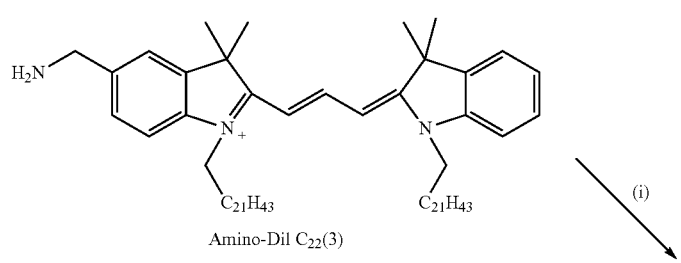

Amino-Dil $C_{22}$(3)

(i)

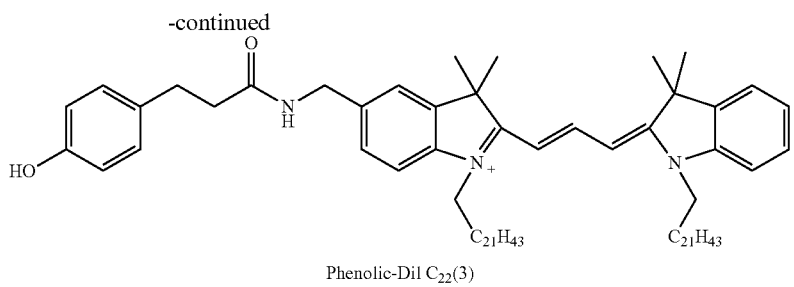

Phenolic-DiI C$_{22}$(3)

In another embodiment, phenolic DiIC$_{14,22}$ is prepared from amino-DiIC$_{14,22}$. Amino-DiI C$_{14,22}$(5) was prepared as previously described [Kopia et al. U.S. Pat. No. 5,667,764] and coupled with 3-(4-hydroxyphenyl)propionic acid in the presence of HBTU in DMF containing triethylamine (Synthetic Pathway 2, below). After stirring at room temperature for 24 h, the mixture was concentrated and purified by silica gel chromatography eluting with increasing amounts of methanol (1% to 5%) in dichloromethane (32% yield). 400 MHz proton NMR (CDCl3): 8.05 (m, 2H), 7.38 (m, 2H), 7.20 (m, 4H), 7.05 (m, 2H), 6.94-7.00 (m, 2H) 6.84 (m, 2H), 6.50 (m, 1H), 6.14 (m, 1H), 6.0 (m, 1H), 5.96 (m, 1H), 4.40 (d, 2H), 3.94 (m, 4H), 2.96 (m, 2H), 2.57 (m, 2H), 1.85-1.60 (m), 1.5-1.2 (m), 0.89 (t, 6H).

lipids bearing sulfonated polysaccharides, cholesterols, tocopherols, lipids with ether-linked fatty acids, lipids with ester-linked fatty acids, polymerized lipids, diacetyl phosphates, dicetyl phosphates, stearylamines, cardiolipin, phospholipids with fatty acids of 6-8 carbons in length, synthetic phospholipids with asymmetric acyl chains, ceramides, non-ionic lipids, sterol aliphatic acid esters, sterol esters of sugar acids, esters of sugar acids, esters of sugar alcohols, esters of sugars, esters of aliphatic acids, saponins, glycerol dilaurate, glycerol trilaurate, glycerol dipalmitate, glycerol, glycerol esters, alcohols of 10-30 carbons in length, 6-(5-cholesten-3beta-yloxy)-1-thio-beta-D-galactopyranoside, digalactosyldiglyceride, 6-(5-cholesten-3beta-yloxy)hexyl-6-amino-6-deoxy-1-thio-beta-D-galacto pyranoside, 6-(5-cholesten-3beta-yloxy)hexyl-6-amino-6-deoxyl-1-thio-alpha-D-manno pyranoside, 12-(((7'-diethylaminocoumarin-3-yl)carbonyl)methylamino)-octalecanoic acid, N-[12-(((7'-

Synthetic Pathway 2

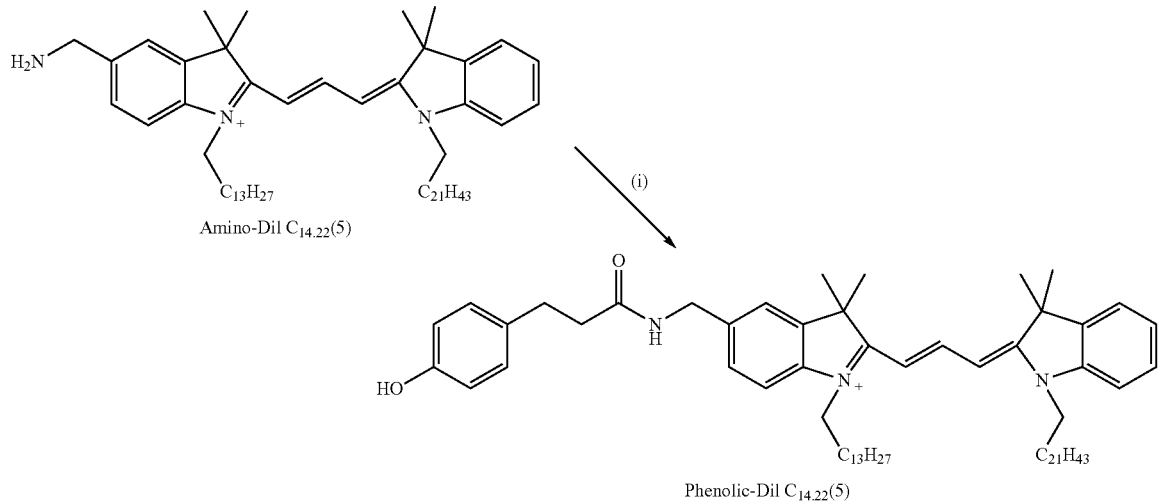

Amino-DiI C$_{14,22}$(5)

Phenolic-DiI C$_{14,22}$(5)

The iodinated phenolic lipid may be incorporated into a vesicle or micelle for administration to a subject. Exemplary vesicles may be formed from a phospholipid bilayer. As used herein, the term "phospholipid" refers to any of a group of fatty compounds comprising phosphoric esters. For example, the phospholipid may be selected from the group consisting of fatty acids, lysolipids, phosphatidylcholines, phosphatidylethanolamines, phosphatidylserines, phosphatidylglycerols, phosphatidylinositols, sphingolipids, glycolipids, glucolipids, sulfatides, glycosphingolipids, phosphatidic acids, palmitic acids, stearic acids, arachidonic acids, oleic acids, lipids bearing polymers, lipids bearing sulfonated monosaccharides, lipids bearing sulfonated disaccharides, lipids bearing sulfonated oligosaccharides, diethylaminocoumarin-3-yl)carbonyl)methylamino) octadeca-noyl]-2-aminopalimitic acid, cholesteryl(4'-trimethylammonio)butanoate, N-succinyldioleoylphosphatidylethanol-amine, 1,2-dioleoyl-sn-glycerol, 1,2-dipalmitoyl-sn-3-succinylglycerol, 1,3-dipalmitoyl-2-succinylglycerol, 1-hexadecyl-2-palmitoylglycerophosphoethanolamine, palmitoylhomocysteine, cationic lipids, N-[1-(2,3-dioleoyloxy)propyl]-N,N,N-trimethylammoium chloride, 1,2-dioleoyloxy-3-(trimethylammonio)propane, 1,2-dioleoyl-3-(4'-trimethylammonio)butanoyl-sn-glycerol, lysophospholipids, lysobisphosphatidic acid (LBPA), semi-lysobisphosphatidic acid (semi-LBPA), cardiolipin, lipids bearing cationic polymers, alkyl phosphonates, alkyl phosphinates, and alkyl phosphites, and combinations thereof. In one embodiment, the phosphatidylcholine is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine, and distearoylphosphatidylcholine. In an embodiment, the phosphatidylethanolamine is selected from the group consisting of dipalmitoylphosphatidylethanolamine and dioleoylphosphatidylethanolamine. In an embodiment, the sphingolipid is sphingomyelin. In an embodiment, the glycolipid is selected from the group consisting of ganglioside GM1 and ganglioside GM2. In an embodiment, in the lipids bearing polymers the polymer is selected from the group consisting of polyethyleneglycol, chitin, hyaluronic acid and polyvinylpyrrolidone. In an embodiment, the sterol aliphatic acid esters are selected from the group consisting of cholesterol sulfate, cholesterol butyrate, cholesterol isobutyrate, cholesterol palmitate, cholesterol stearate, lanosterol acetate, ergosterol palmitate, and phytosterol n-butyrate. In an embodiment, the sterol esters of sugar acids are selected from the group consisting of cholesterol glucuronide, lanosterol glucuronide, 7-dehydrocholesterol glucuronide, ergosterol glucuronide, cholesterol gluconate, lanosterol gluconate, and ergosterol gluconate. In an embodiment, the esters of sugar acids and the esters of sugar alcohols are selected from the group consisting of lauryl glucuronide, stearoyl glucuronide, myristoyl glucuronide, lauryl gluconate, myristoyl gluconate, and stearoyl gluconate. In an embodiment, the esters of sugars and the esters of aliphatic acids are selected from the group consisting of sucrose laurate, fructose laurate, sucrose palmitate, sucrose stearate, glucuronic acid, gluconic acid, accharic acid, and polyuronic acid. In an embodiment, the saponins are selected from the group consisting of sarsasapogenin, smilagenin, hederagenin, oleanolic acid, and digitoxigenin. In an embodiment, the glycerol esters are selected from the group consisting of glycerol tripalmitate, glycerol distearate, glycerol tristearate, glycerol dimyristate, glycerol and trimyristate. In an embodiment, the alcohols are of 10-30 carbon length and are selected from the group consisting of n-decyl alcohol, lauryl alcohol, myristyl alcohol, cetyl alcohol, and n-octadecyl alcohol. In an embodiment, in the lipids bearing cationic polymers the cationic polymers are selected from the group consisting of polylysine and polyarginine. In another embodiment, the phospholipid is selected from the group consisting of dipalmitoylphosphatidylcholine, dipalmitoylphosphatidylethanolamine, and dipalmitoylphosphatidic acid, and structural analogs thereof. In one embodiment, the phospholipid is dioleoylphosphatidylserine (1,2-dioleoyl-sn-glycero-3-phospho-L-serine; "DOPS").

The size of the vesicles or micelles can also vary according to the present disclosure. In some embodiments, the average diameter of the vesicles or micelles may range from about 10 nanometers (nm) to about 1000 nm in diameter. In other embodiments, the average diameter of the vesicles or micelles may range from about 10 nm to about 500 nm. In other embodiments, the average diameter of the vesicles or micelles may range from about 10 nm to about 350 nm. In other embodiments, the average diameter of the vesicles or micelles may range from about 10 nm to about 200 nm. In other embodiments, the average diameter of the vesicles or micelles may range from about 10 nm to about 150 nm. In other embodiments, the average diameter of the vesicles or micelles may range from about 10 nm to about 100 nm. In other embodiments, the average diameter of the vesicles or micelles may range from about 10 nm to about 75 nm. In other embodiments, the average diameter of the vesicles or micelles may range from about 10 nm to about 50 nm. In other embodiments, the average diameter of the vesicles or micelles may range from about 25 nm to about 500 nm. In other embodiments, the average diameter of the vesicles or micelles may range from about 25 nm to about 350 nm. In other embodiments, the average diameter of the vesicles or micelles may range from about 25 nm to about 200 nm. In other embodiments, the average diameter of the vesicles or micelles may range from about 25 nm to about 150 nm. In other embodiments, the average diameter of the vesicles or micelles may range from about 25 nm to about 100 nm. In other embodiments, the average diameter of the vesicles or micelles may range from about 25 nm to about 75 nm. In other embodiments, the average diameter of the vesicles or micelles may range from about 25 nm to about 50 nm. In other embodiments, the average diameter of the vesicles or micelles may range from about 50 nm to about 500 nm. In other embodiments, the average diameter of the vesicles or micelles may range from about 50 nm to about 350 nm. In other embodiments, the average diameter of the vesicles or micelles may range from about 50 nm to about 250 nm. In other embodiments, the average diameter of the vesicles or micelles may range from about 50 nm to about 200 nm. In other embodiments, the average diameter of the vesicles or micelles may range from about 50 nm to about 150 nm. In other embodiments, the average diameter of the vesicles or micelles may range from about 50 nm to about 100 nm. In other embodiments, the average diameter of the vesicles or micelles may range from about 50 nm to about 75 nm. In other embodiments, the average diameter of the vesicles or micelles is approximately 10 nm. In other embodiments, the average diameter of the vesicles or micelles is approximately 25 nm. In other embodiments, the average diameter of the vesicles or micelles is approximately 50 nm. In other embodiments, the average diameter of the vesicles or micelles is approximately 75 nm. In other embodiments, the average diameter of the vesicles or micelles is approximately 100 nm. In other embodiments, the average diameter of the vesicles or micelles is approximately 150 nm. In other embodiments, the average diameter of the vesicles or micelles is approximately 200 nm. The size of the vesicles or micelles can be adjusted, if desired, by a variety of procedures including, for example, shaking, microemulsification, vortexing, extrusion, filtration, sonication, homogenization, repeated freezing and thawing cycles, extrusion under pressure through pores of defined size, or other methods known to those skilled in the art.

Another aspect of the invention is directed to the use of the cosolvent composition in methods of iodinating phenolic lipids using an aqueous-based iodination protocol.

During use, a phenolic lipid is solubilized in a volume of cosolvent composition that includes an alcohol portion and an aqueous portion, as described above. In an exemplary protocol, about 100 micrograms of a phenolic lipid is solubilized in about 100 microliters of the cosolvent composition. An iodide ion is added to the cosolvent composition. For example, the iodide ion may be added as a salt dissolved in an aqueous media that optionally contains at least one of a salt and a buffer. The iodide ion may be added either before or after the phenolic lipid is solubilized. The mixture is then processed utilizing an aqueous-based iodination protocol.

An exemplary aqueous-based iodination protocol is performed in a reaction tube that has been pre-coated with an iodination reagent. In a preferred embodiment, the iodination reagent is a mild oxidizer that is capable of resulting in the formation of iodide ions from molecular iodine. An exemplary mild oxidizer is 1,3,4,6-tetrachloro-3α, 6α-diphenylglycouracil, which is insoluble in aqueous media. An example of a pre-coated iodination tube is marketed as the Pierce® Pre-Coated Iodination Tube.

The mixture of the cosolvent composition, phenolic lipid, and iodide ion is added to the iodination tube and incubated for a period of time sufficient to result in the iodination of the phenolic lipid. The mixture may be incubated for a period of time ranging between about 5 minutes and 30 minutes, and alternatively between about 5 minutes and about 20 minutes, and alternatively for about 15 minutes. During the incubation, the mixture may be periodically agitated such as by sonication, vortexing, or by hand shaking. The reaction may be terminated by removing the mixture from the iodination reaction tube. The iodinated phenolic lipid may be recovered by routine methods such as by elution through a C4 reverse phase column. The incorporation of iodide into the phenolic lipid may be verified using routine processes such as by mass spectrometry analysis. The reaction is preferably conducted at around 37 degrees Celsius (plus or minus 5 degrees) and at a pH in the range from about pH 6 to about pH 8.

In an alternative method, an aqueous solution of the iodide salt may be activated in the iodination reaction tube for a period of time before being removed from the tube and added to the phenolic lipid to be iodinated solubilized in the cosolvent.

An additional aspect of the invention is directed to iodinated phenolic lipids wherein the lipid portion includes a fluorophore coupled to at least one lipophilic anchor, and preferably a pair of lipophilic anchors. Exemplary phenolic lipids include phenolic carbocyanine dyes, preferably $DilC_{22}$ and $DilC_{14,22}$. The phenolic lipids are iodinated at least one of six carbons forming the phenolic ring. The iodinated phenolic lipid may be iodinated at 1, 2, or 3 carbons along the phenolic ring.

Another aspect of the invention is directed to methods of treating a disease with iodinated phenolic lipids prepared in accordance with embodiments of the present invention. In particular, the phenolic lipids may be iodinated with an isotope of iodine for imaging, antitumor activity, or both imaging and antitumor activity. The iodinated phenolic lipids may be incorporated into a vesicle as described herein. The iodinated phenolic lipid containing vesicle may include a secondary component that targets the tissue of interest. For example, the vesicle may also include an antibody, or other macromolecule capable of targeting the tissue of interest, such as saposin C (SapC). The iodinated phenolic lipid containing vesicle may be administered to the subject, such as by intravenous injection in an amount effective to image the target tissue or an amount effective to have an antitumor effect on the target tissue. In an embodiment, the target tissue is a cancer, such as a solid cancer. An exemplary cancer that may be treated with embodiments of the iodinated phenolic lipid containing vesicle is glioblastoma.

Example 1

Figure 3:
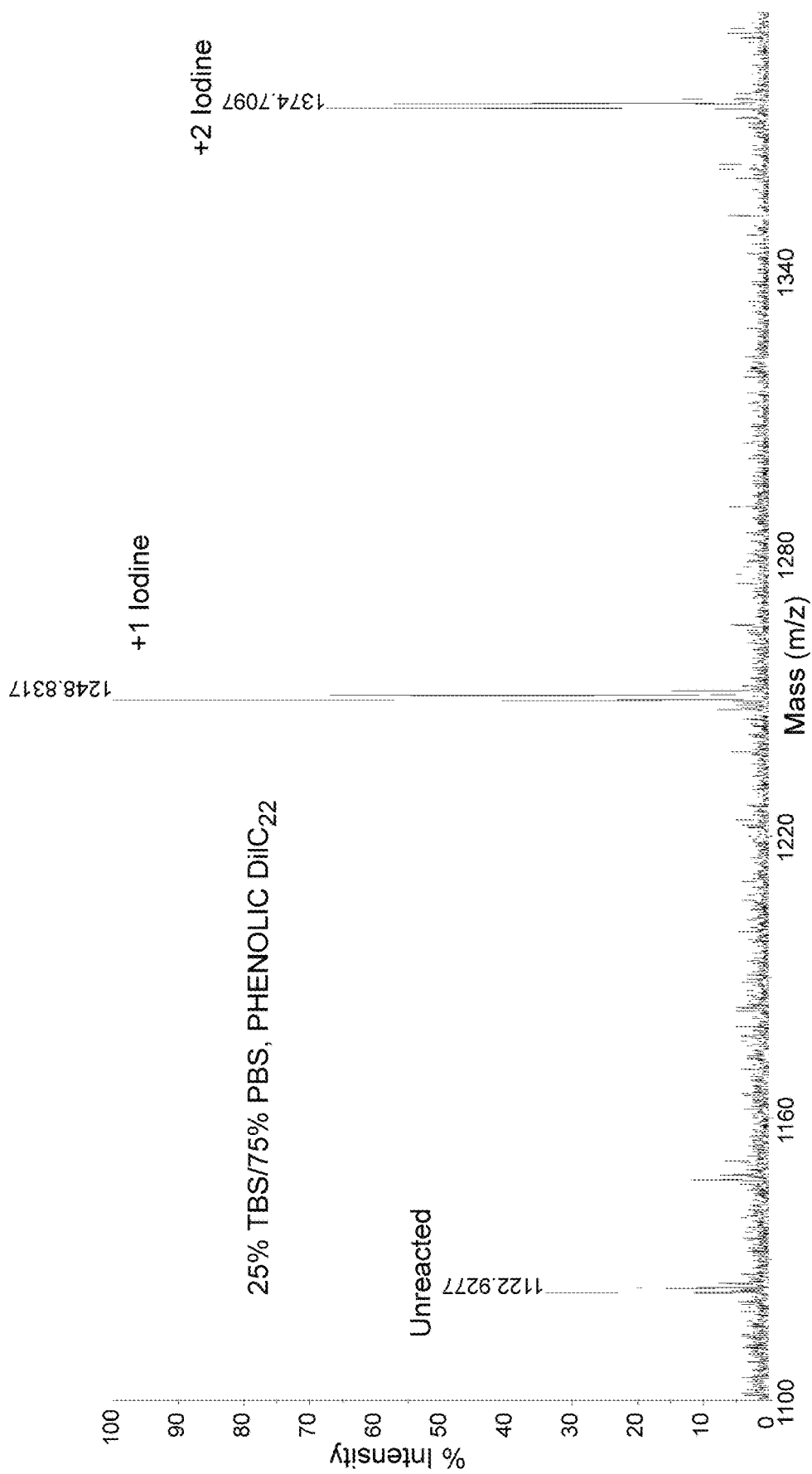
FIG. 3 is a tracing from the mass spectrometry analysis of a phenolic lipid suspended in PBS without a cosolvent.

Several organic solvents were evaluated for usefulness in the cosolvent composition. The evaluated solvents included tertiary-butyl alcohol (TBA) (FIGS. 1B-2), dimethylsulfoxide (DMSO) (FIGS. 4 and 8), chloroform (FIGS. 5 and 8), ethanol (FIG. 6), tetrahydrofuran (THF) (FIG. 7), isopropyl alcohol, 2-methyl-2-butanol, 2-methyl-1-butanol, 2-butanol, n-butanol, and pentanol. PBS without any organic solvents was evaluated as a control (FIGS. 1A and 3). The organic solvents were mixed with aqueous media (PBS or water) to form a cosolvent composition as shown in TABLE 1.

The cosolvent formulations were evaluated using the Pierce® Pre-Coated Iodination Tube protocol for direct iodination of compounds. Briefly, the about 100 micrograms of phenolic lipid (i.e., phenolic $DilC_{14,22}$ or phenolic $DilC_{22}$) was suspended in about 100 microliters of the cosolvent composition being evaluated. PBS containing NaI was added to the mixture to a final concentration of 1 mM. The mixture was briefly sonicated and added to a Pierce® Pre-Coated Iodination Tube and incubated for 15 minutes with periodic agitation. Labeled compounds were recovered by elution through a Sep-Pak (C4 reverse phase) chromatography column. Incorporation of iodine into the phenolic lipids was evaluated by MALDI analysis.

| Organic Solvent | Aqueous Media | Or. Sol.:Aq. Med. Ratio | Phenolic lipid tested | Miscible in Aq. Med. (Yes or | Dissolve Phenolic Lipid | Iodination (Yes or No) |
|---|---|---|---|---|---|---|
| Control: No organic solvent | PBS | 0:100 | $PhenDilC_{14,22}$ or $PhenDilC_{22}$ | NA | No | No |
| DMSO | PBS | 90:10 | $PhenDilC_{22}$ | Yes | Yes | No |
| Chloroform | PBS | 50:50 | $PhenDilC_{22}$ | Yes | Yes | No |
| Ethanol | PBS | 70:30 | $PhenDilC_{22}$ | Yes | Yes | No |
| THF | PBS | 91:9 | $PhenDilC_{22}$ | Yes | Yes | No |
| DMSO/Chloroform | PBS | 10:80:10 | $PhenDilC_{22}$ | YES | Yes | No |
| TBA | PBS | 10:90 | $PhenDilC_{14,22}$ | Yes | Yes | Yes |
| TBA | PBS | 25:75 | $PhenDilC_{14,22}$ | Yes | Yes | Yes |
| TBA | PBS | 50:50 | $PhenDilC_{14,22}$ | Yes | Yes | Yes |
| TBA | PBS | 25:75 | $PhenDilC_{22}$ | Yes | Yes | Yes |
| Isopropanol | PBS | 25:75 | $PhenDilC_{22}$ | Yes | Yes | Yes |
| 2-methyl-2-butanol | water | 25:75 | $PhenDilC_{22}$ | Yes | Yes | No |
| 2-methyl-1-butanol | water | 25:75 | $PhenDilC_{22}$ | No | No | No |
| 2-butanol | water | 25:75 | $PhenDilC_{22}$ | Yes | Yes | No |
| n-butanol | water | 25:75 | $PhenDilC_{22}$ | No | No | No |
| pentanol | water | 25:75 | $PhenDilC_{22}$ | No | No | No |

Figure 1C:
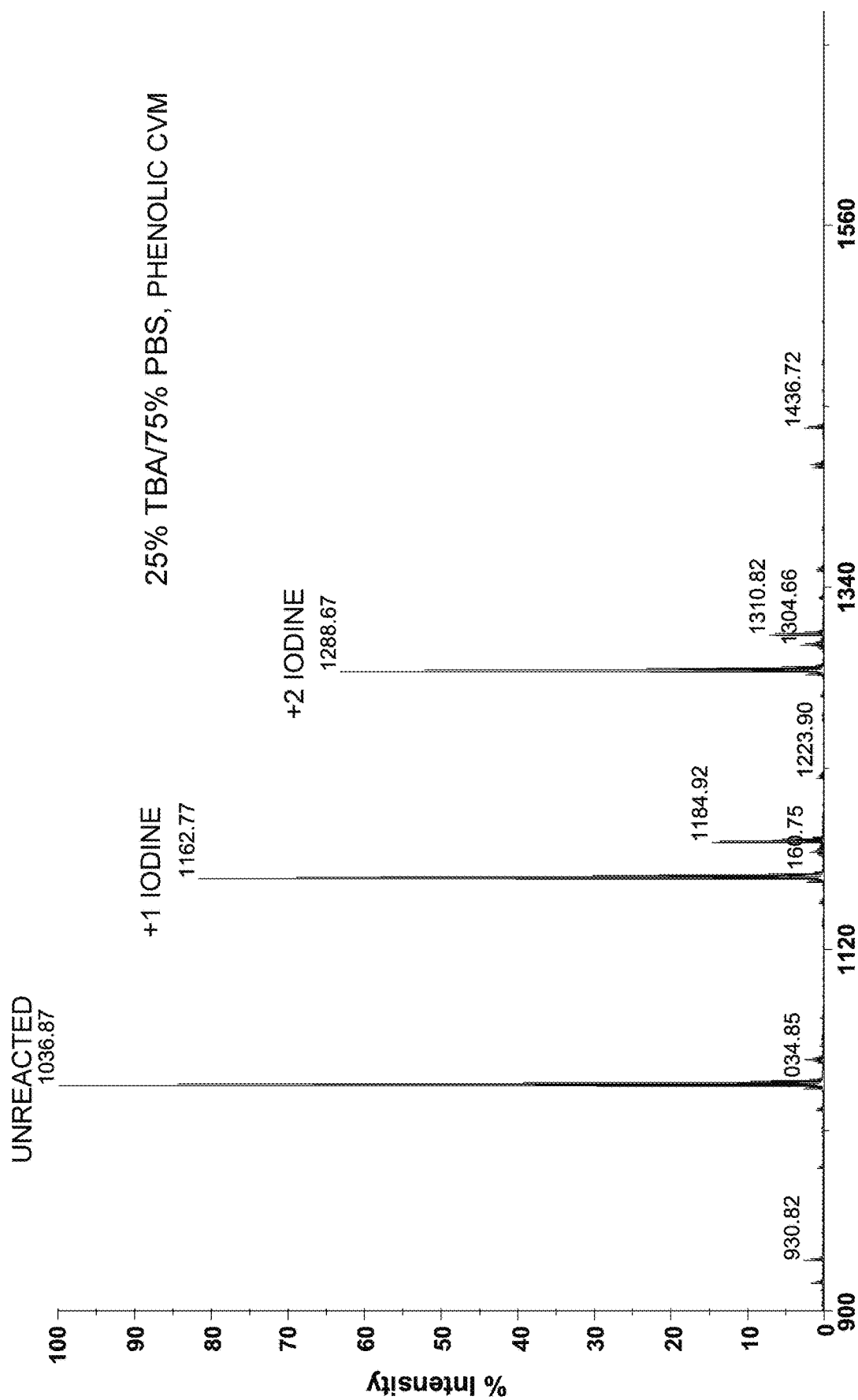
FIG. 1C is a tracing from the mass spectrometry analysis of a phenolic lipid iodinated in a cosolvent composition having a 75:25 PBS to TBA (vol:vol) ratio in accordance with embodiments of the invention.
Figure 1D:
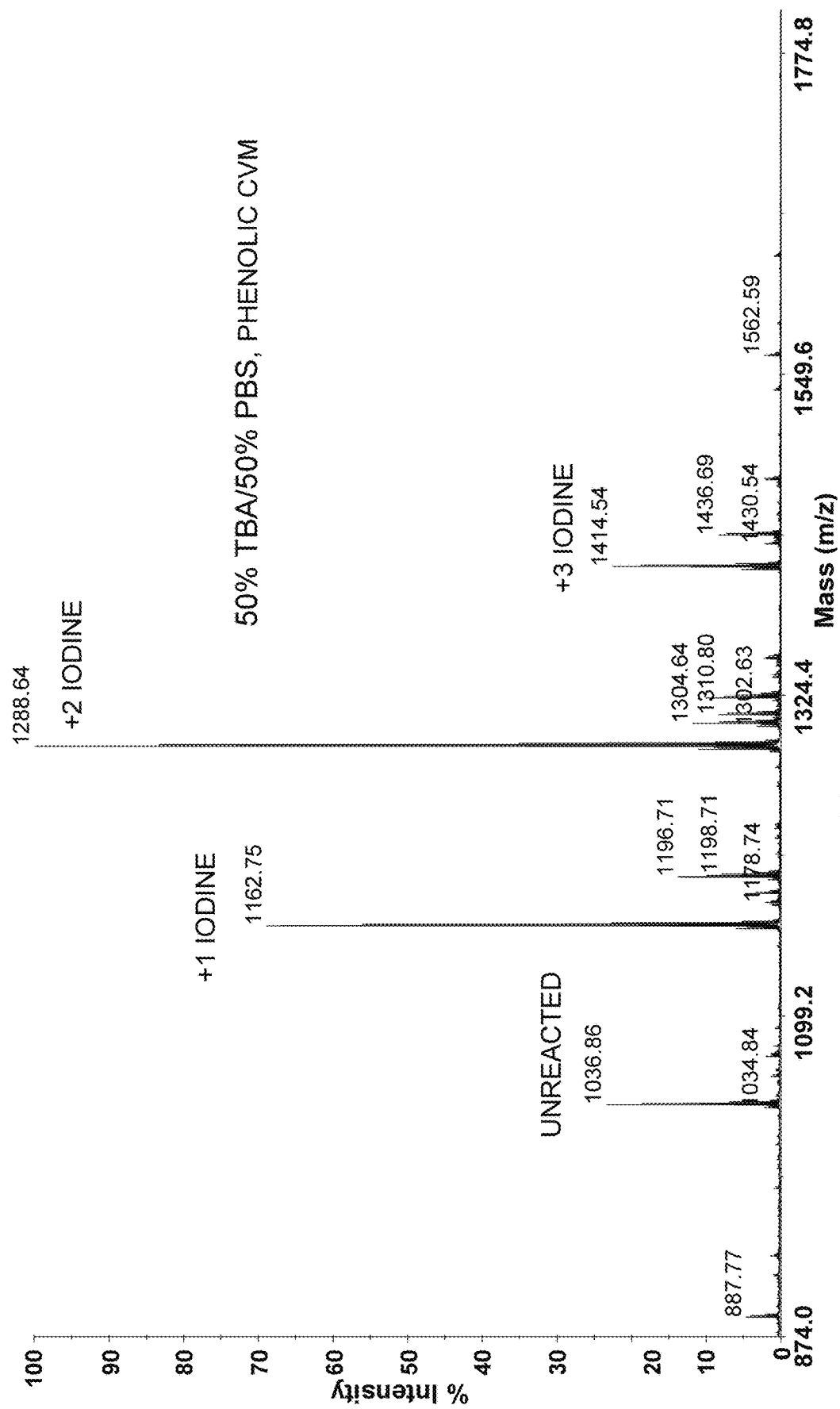
FIG. 1D is a tracing from the mass spectrometry analysis of a phenolic lipid iodinated in a cosolvent composition having a 50:50 PBS to TBA (vol:vol) ratio in accordance with embodiments of the invention.

The mass spectrometry tracings in FIGS. 1A and 3 demonstrate phenolic lipids (either phenolic DilC14,22 or phenolic $DilC_{22}$) suspended in an aqueous media without a co-solvent were not iodinated in the aqueous-based iodination protocol utilizing Pierce® Pre-Coated Iodination Tubes. FIGS. 1A-1D demonstrate that an exemplary cosolvent composition that includes TBA and PBS yields iodinated phenolic DilC$_{14,22}$ over a range of alcohol to water (vol:vol) ratios from 10:90 to 50:50 in the aqueous-based iodination protocol. The 10:90 TBA:PBS formulation results in about 35.5 percent of the phenolic DilC$_{14,22}$ being iodinated, with about 24.5 percent being iodinated in 1 position and about 11 percent being iodinated in a second position (FIG. 1B). The 25:75 TBA:PBS formulation results in about 58.8 percent of the phenolic DilC$_{14,22}$ being iodinated, with 33.3 percent being iodinated in a first position and 25.5 percent being iodinated in a second position (FIG. 1C). The 50:50 TBA:PBS formulation results in about 89.2 percent of the phenolic DilC$_{14,22}$ being iodinated, with about 32.1 percent being iodinated in a first position, 47.2 percent being iodinated in a second position, and 9.9 percent being iodinated in a third position (FIG. 1D).

Similarly, FIG. 2 demonstrates that the 25:75 TBA:PBS formulation results in about 85.3 percent of the phenolic DilC$_{22}$ being iodinated, with about 50.8 percent being iodinated in a first position and about 34.5 percent being iodinated in a second position.

Figure 7:
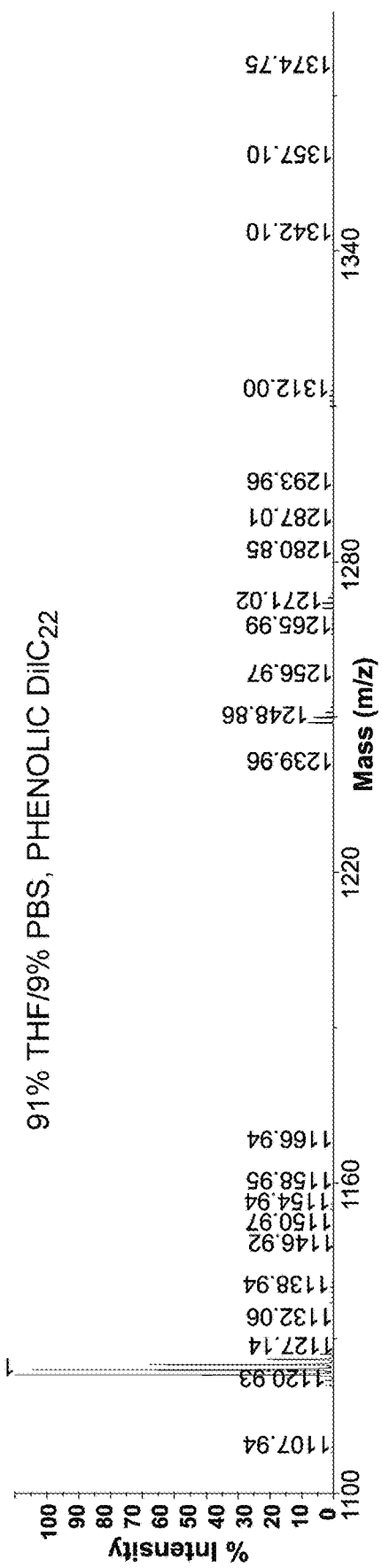
FIG. 7 is a tracing from the mass spectrometry analysis of a phenolic lipid processed with a protocol utilizing a cosolvent that included 91% THF and 9% PBS.
Figure 8:
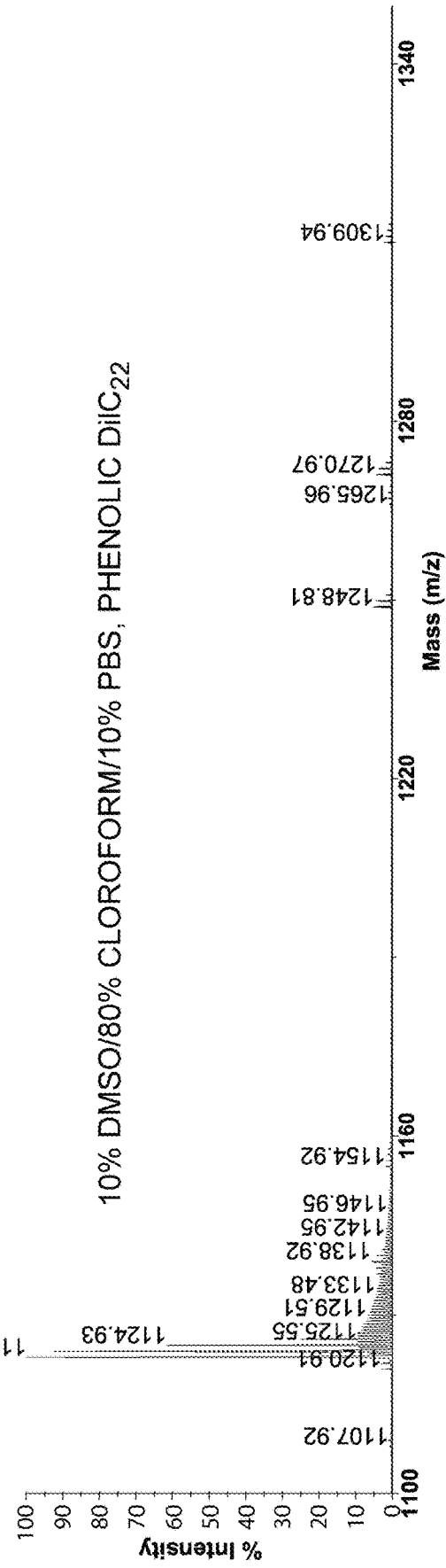
FIG. 8 is a tracing from the mass spectrometry analysis of a phenolic lipid processed with a protocol utilizing a cosolvent that included 10% DMSO, 80% chloroform, and 10% PBS.

Not all cosolvent formulations tested resulted in the iodination of a phenolic lipid. FIG. 4 demonstrates that the 90:10 DMSO:PBS formulation fails to result in the iodination of the phenolic lipid. FIG. 5 demonstrates that the 50:50 chloroform:PBS formulation also fails to result in the iodination of the phenolic lipid. FIG. 6 demonstrates that the 70:30 ethanol:PBS formulation also fails to result in the iodination of the phenolic lipid. FIG. 7 demonstrates that the 91:9 THF:PBS formulation also fails to result in the iodination of the phenolic lipid. FIG. 8 demonstrates that the 10:80:10 DMSO:chloroform:PBS formulation also fails to result in the iodination of the phenolic lipid.

The data shown in Table 1 and FIGS. 1-8 demonstrate that cosolvents having either TBA or isopropanol as the alcohol component are capable of resulting in the iodination of phenolic lipids in aqueous-based iodination protocols. However, not all organic solvents are capable of resulting iodination of phenolic lipids when used in an aqueous-based iodination protocol. In particular, the organic solvent must be miscible in aqueous media and must be capable of dissolving the phenolic lipid. The data also demonstrate that not all organic solvents that are miscible in water and capable of dissolving phenolic lipids are also capable of resulting in the iodination of phenolic lipids in aqueous-based iodination protocols.

Without being bound to any particular theory, it is hypothesized that alcohols, such as TBA and isopropanol, that result in iodination of phenolic lipids in aqueous-based iodination protocols expose the phenol group on the phenolic lipid to the iodide ion for iodination in the cosolvent composition, whereas the other organic solvents tested were incapable of efficiently exposing the phenol to allow the reaction to proceed.

An aspect of the invention is directed to methods of treating a disease, such as cancer, or imaging a disease tissue or diagnosing a subject as having a disease using a phenolic lipid, and in particular with an iodinated phenolic lipid. In an embodiment, the phenolic lipid is iodinated with a I131.

Example 2

Figure 9:
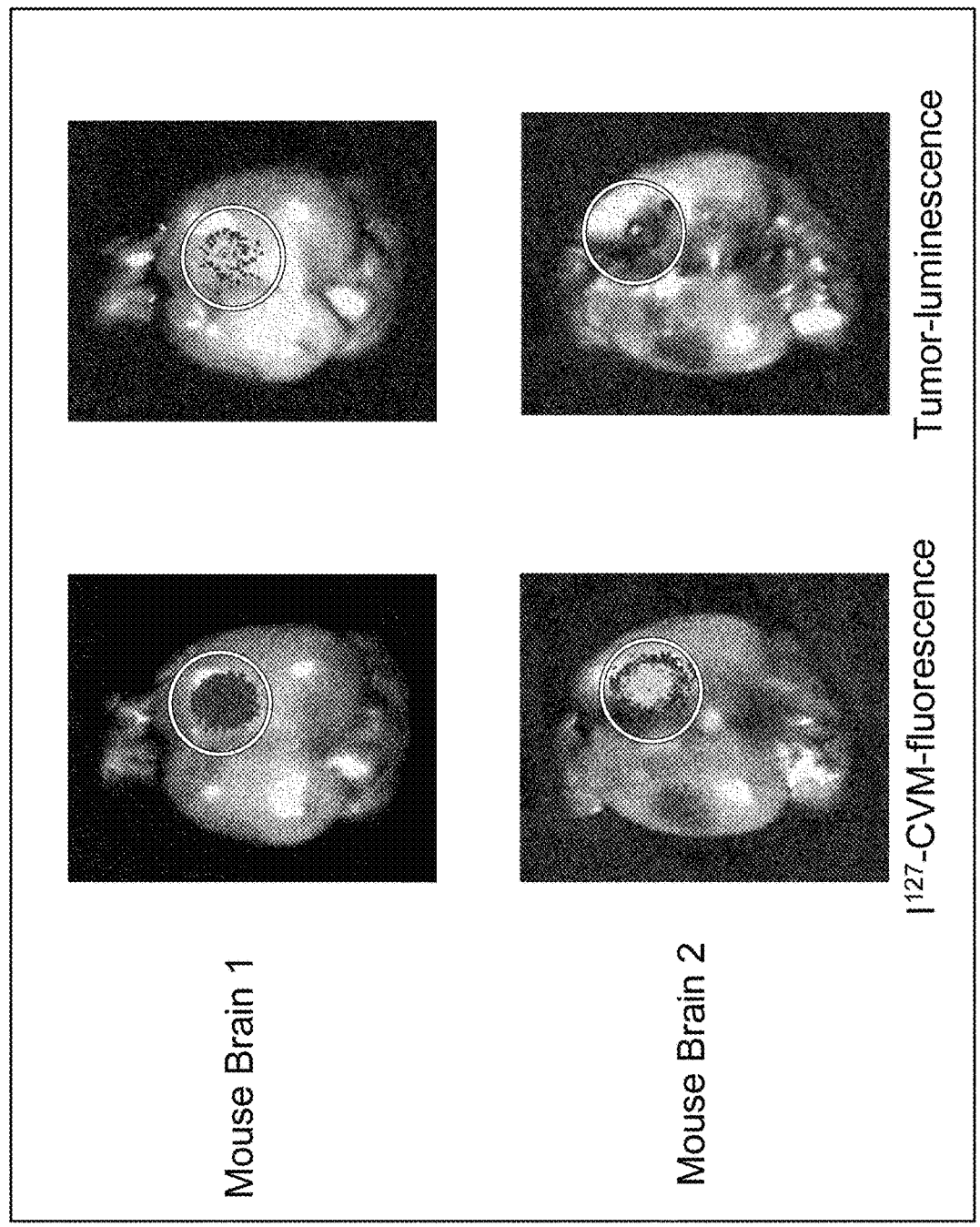
FIG. 9 is a series of PET images demonstrating the co-localization of I-127 fluorescence and tumor luminescence in a tumor in mousebrains.

Lipid bilayer nanovesicles containing I-127 labeled or I-125 labeled phenolic DilC$_{14,22}$ and SapC-DOPS were introduced into a mouse brain tumor model. In particular, mice were intravenously injected with the I-127 labeled or I-125 labeled phenolic DilC$_{14,22}$ and SapC-DOPS nanovesicles. As illustrated in FIG. 9, the nanovesicles targeted the tumor and delivered the I-127 labeled phenolic DilC$_{14,22}$ to the tumor. In a follow up study, mice bearing intracranial glioblastoma (TUMOR) or saline were intravenously injected with I-125 labeled phenolic DilC$_{14,22}$ and SapC-DOPS nanovesicles and their brains were removed at 1 hour, 3 hours, 6 hours, and 24 hours after injection. The brains of the TUMOR mice had significantly elevated levels of the labeled phenolic DilC$_{14,22}$ at each time point when compared to non-tumor mice. These data demonstrate that I-127 and I-125 labeled phenolic DilC$_{14,22}$, when coupled in a nanovesicle with SapC-DOPS, may be useful for imaging and potentially treating solid tumors, such as those found in the brain and other tissues. Accordingly an aspect of the invention is directed to treatment of medical conditions, such as cancers, by administering to a subject an iodinated phenolic lipid in an amount effective to treat the condition.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A composition comprising a phenol group conjugated to a lipid group, wherein the lipid group includes a lipid portion coupled to a fluorophore, and wherein the lipid group is selected from the group consisting of DilC$_{22}$, DilC$_{14,22}$, and combinations thereof.

2. The composition of claim 1 further comprising a vesicle or a micelle wherein said phenolic lipid is incorporated into at least one of the vesicle or micelle.

3. The composition of claim 2 wherein the vesicle or micelle includes saposin C ("SapC") and dioleoylphosphatidylserine (DOPS).

4. A composition comprising:
a phenolic lipid and at least one of a vesicle or a micelle, wherein the phenolic lipid includes a lipid group conjugated to a phenol group and the lipid group includes a lipid portion coupled to a fluorophore, and wherein the lipid group is selected from the group consisting of DilC$_{22}$, DilC$_{14,22}$, and combinations thereof.

5. The composition of claim 4 wherein the at least of a vesicle or a micelle includes SapC and DOPS.

6. The composition of claim 4 wherein the phenolic lipid group is labeled with a radioactive isotope of iodine.

* * * * *